US012339282B2

(12) United States Patent
Liu et al.

(10) Patent No.: US 12,339,282 B2
(45) Date of Patent: Jun. 24, 2025

(54) CORONAVIRUS ANTIBODY DETECTION KIT BASED ON MAGNETIC PARTICLE CHEMILUMINESCENCE

(71) Applicant: Dynamiker Biotechnology (Tianjin) Co, Ltd., Binhai New Area Tianjin (CN)

(72) Inventors: Chunlong Liu, Binhai New Area Tianjin (CN); Zhou Zhang, Binhai New Area Tianjin (CN); Shaohua Ma, Binhai New Area Tianjin (CN); Jiashun Wang, Binhai New Area Tianjin (CN); Yan Su, Binhai New Area Tianjin (CN); Zeqi Zhou, Binhai New Area Tianjin (CN)

(73) Assignee: Dynamiker Biotechnology (Tianjin) Co., Ltd., Binhai New Area Tianjin (CN)

( * ) Notice: Subject to any disclaimer, the term of this patent is extended or adjusted under 35 U.S.C. 154(b) by 141 days.

(21) Appl. No.: 17/436,791

(22) PCT Filed: Mar. 24, 2021

(86) PCT No.: PCT/CN2021/082727
§ 371 (c)(1),
(2) Date: Sep. 7, 2021

(87) PCT Pub. No.: WO2022/121151
PCT Pub. Date: Jun. 16, 2022

(65) Prior Publication Data
US 2023/0296601 A1  Sep. 21, 2023

(30) Foreign Application Priority Data
Dec. 10, 2020 (CN) .......... 202011432236.4

(51) Int. Cl.
*G01N 33/569* (2006.01)
*G01N 21/76* (2006.01)
(Continued)

(52) U.S. Cl.
CPC ....... *G01N 33/56983* (2013.01); *G01N 21/76* (2013.01); *G01N 33/532* (2013.01);
(Continued)

(58) Field of Classification Search
None
See application file for complete search history.

(56) References Cited

U.S. PATENT DOCUMENTS

| 10,844,442 B1 | 11/2020 | Barnhizer et al. |
| 2020/0291490 A1 | 9/2020 | Jolly et al. |
| 2023/0296601 A1* | 9/2023 | Liu ............ G01N 21/76 435/5 |

FOREIGN PATENT DOCUMENTS

| CN | 1829736 A | 9/2006 |
| CN | 108350050 A | 7/2018 |

(Continued)

OTHER PUBLICATIONS

Derwent database translation of Chen et al. CN_101165487—2008.*
(Continued)

*Primary Examiner* — Shanon A. Foley
(74) *Attorney, Agent, or Firm* — Morse, Barnes-Brown & Pendleton, P.C.; Sean D. Detweiler, Esq.

(57) ABSTRACT

The present application provides a novel coronavirus antibody detection kit based on magnetic particle chemiluminescence. The detection kit includes: streptavidin magnetic particles, biotin-labeled novel coronavirus antigens, an acridine sulfonamide-labeled secondary antibody, a sample diluent and a quality control material; wherein the biotin-
(Continued)

labeled novel coronavirus antigens include a recombinant nucleocapsid protein and a recombinant spike protein S1. The sample to be tested, the biotin-labeled antigens and the streptavidin magnetic particles are mixed, incubated and washed, and then the acridine sulfonamide-labeled antibody is added to form a magnetic particle-streptavidin-biotin-antigen-novel coronavirus antibody-secondary antibody complex, and then the luminous intensity is detected to qualitatively determine the sample to be tested.

9 Claims, 1 Drawing Sheet

Specification includes a Sequence Listing.

(51) Int. Cl.
*G01N 33/532* (2006.01)
*G01N 33/543* (2006.01)
*G01N 33/563* (2006.01)

(52) U.S. Cl.
CPC ..... *G01N 33/54326* (2013.01); *G01N 33/563* (2013.01); *G01N 2469/20* (2013.01)

(56) References Cited

FOREIGN PATENT DOCUMENTS

| CN | 108431018 A | 8/2018 |
|----|-------------|--------|
| CN | 109239356 A | 1/2019 |
| CN | 110146692 A | 8/2019 |
| CN | 111187354 A | 5/2020 |
| CN | 111196857 A | 5/2020 |
| CN | 111217920 A | 6/2020 |
| CN | 111273016 A | 6/2020 |
| CN | 111337682 A | 6/2020 |
| CN | 111393532 A | 7/2020 |
| CN | 111505283 A | 8/2020 |
| CN | 111551743 A | 8/2020 |
| CN | 111562368 A | 8/2020 |
| CN | 111607003 A | 9/2020 |
| CN | 111848751 A | 10/2020 |
| CN | 111848752 A | 10/2020 |
| CN | 111848754 A | 10/2020 |
| CN | 111856004 A | 10/2020 |
| CN | 112028975 A | 12/2020 |
| CN | 112229994 A | 1/2021 |

OTHER PUBLICATIONS

Derwent database translation of Qui et al. (CN_108872594—2018).*
Derwent database translation of Ma et al. (CN117388490—2024).*
"NSP-SA-NHS". MedChemExpress, MCE®, found at: https://www.medchemexpress.com/nsp-sa-nhs.html?srsltid=AfmBOooi9n6vDEPeL4P012fqph_O5z1Ad1KITYq8j6VKb4b1CyCuJ_6—2024).*
Xiang et al. (BMC Infectious Diseases. Dec. 2020; 20:1-7).*
Derwent translation of Chen et al. (CN 111217920, published Nov. 11, 2020).*
Derwent translation of Yao et al. (CN 102565405, published Jul. 2012).*
Ponnuswamy et al. (Nature communications. May 31, 2017;8(1):15654).*
Cai, et al., "A Peptide-Based Magnetic Chemiluminescence Enzyme Immunoassay for Serological Diagnosis of Coronavirus Disease 2019 (COVID-19)," *J. Infect. Dis.*, pp. 1-19, Published online May 8, 2020.
Feng, et al., "Expression of Predicted B Cell Epitope Peptide in S2 Subunit of SARS Coronavirus Spike Protein in *E. coli* and Identification of its Mimic Antigenicity," *Chin. J. Cell. Mol. Immunol.*, 23(2):113-116, (2007).
Hatmal, et al., "Comprehensive Structural and Molecular Comparison of Spike Proteins of SARS-CoV-2, SARS-CoV and MERS-CoV, and Their Interactions with ACE2," *Cells*, 9:1-37, (2020).
Huang, et al., "Prediction of Secondary Structure and B- and T-Cell Epitopes of σB and σC Proteins of Avian Reovirus," *China Animal Husbandry & Veterinary Medicine*, 43(11):2880-2885, (2016).
Tian, et al., "Roles of SARS-CoV-2 N Protein and S Protein Antibody Determinations in the Diagnosis of COVID-19," *Laboratory Medicine*, 35(11):1136-1139, (Nov. 2020).
Zhang, et al., "Evaluation of Recombinant Nucleocapsid and Spike Protein for Serological Diagnosis of Novel Coronavirus Disease 2019 (COVID-19)," MedRxiv 2020.03.17.20036954; doi: https://doi.org/10.1101/2020.03.17.20036954; pp. 1-28, (posted Sep. 1, 2020).
International Search Report from PCT/CN2021/082727, dated Aug. 27, 2021.

* cited by examiner

SEQUENCE LISTING

```
<160> NUMBER OF SEQ ID NOS: 4

<210> SEQ ID NO 1
<211> LENGTH: 249
<212> TYPE: PRT
<213> ORGANISM: Artificial sequence
<220> FEATURE:
<223> OTHER INFORMATION: recombinant nucleocapsid protein

<400> SEQUENCE: 1

Gly Gly Pro Ser Asp Ser Thr Gly Ser Asn Gln Asn Gly Glu Arg Ser
1               5                   10                  15

Gly Ala Arg Ser Lys Gln Arg Arg Pro Gln Gly Leu Pro Asn Asn Thr
            20                  25                  30

Pro Pro Pro Ala Leu Asn Thr Pro Lys Asp His Ile Gly Thr Arg Asn
        35                  40                  45

Pro Ala Asn Asn Pro Pro Gly Phe Tyr Ala Glu Gly Ser Arg Gly
    50                  55                  60

Gly Ser Gln Ala Ser Ser Arg Ser Ser Ser Arg Ser Arg Asn Ser Ser
65                  70                  75                  80

Arg Asn Ser Thr Pro Gly Ser Ser Arg Gly Thr Ser Pro Ala Arg Met
                85                  90                  95

Ala Gly Asn Gly Gly Asp Pro Pro Leu Glu Ser Lys Met Ser Gly
            100                 105                 110

Lys Gly Gln Gln Gln Gln Gly Gln Thr Val Thr Lys Lys Ser Ala Ala
        115                 120                 125

Glu Ala Ser Lys Lys Pro Arg Gln Lys Arg Thr Ala Thr Lys Pro Pro
    130                 135                 140

Pro Ala Phe Gly Arg Arg Gly Pro Glu Gln Thr Gln Gly Asn Phe Gly
145                 150                 155                 160

Asp Gln Glu Leu Ile Arg Gln Gly Thr Asp Tyr Lys His Trp Pro Pro
                165                 170                 175
```

```
Pro Lys Leu Asp Asp Lys Asp Pro Asn Phe Lys Asp Gln Pro Pro
            180                 185                 190
Pro Thr Phe Pro Pro Thr Glu Pro Lys Asp Lys Lys Lys Lys Ala Asp
        195                 200                 205
Glu Thr Gln Ala Leu Pro Gln Arg Gln Lys Lys Gln Gln Thr Val Pro
    210                 215                 220
Pro Pro Leu Asp Asp Phe Ser Lys Gln Leu Gln Gln Ser Met Ser Ser
225                 230                 235                 240
Ala Asp Ser Thr Gln Ala Lys Lys Lys
                245
```

<210> SEQ ID NO 2
<211> LENGTH: 419
<212> TYPE: PRT
<213> ORGANISM: Artificial sequence
<220> FEATURE:
<223> OTHER INFORMATION: original nucleocapsid protein

<400> SEQUENCE: 2

```
Met Ser Asp Asn Gly Pro Gln Asn Gln Arg Asn Ala Pro Arg Ile Thr
1               5                   10                  15
Phe Gly Gly Pro Ser Asp Ser Thr Gly Ser Asn Gln Asn Gly Glu Arg
                20                  25                  30
Ser Gly Ala Arg Ser Lys Gln Arg Arg Pro Gln Gly Leu Pro Asn Asn
            35                  40                  45
Thr Ala Ser Trp Phe Thr Ala Leu Thr Gln His Gly Lys Glu Asp Leu
        50                  55                  60
Lys Phe Pro Arg Gly Gln Gly Val Pro Ile Asn Thr Asn Ser Ser Pro
65                  70                  75                  80
Asp Asp Gln Ile Gly Tyr Tyr Arg Arg Ala Thr Arg Arg Ile Arg Gly
                85                  90                  95
Gly Asp Gly Lys Met Lys Asp Leu Ser Pro Arg Trp Tyr Phe Tyr Tyr
                100                 105                 110
Leu Gly Thr Gly Pro Glu Ala Gly Leu Pro Tyr Gly Ala Asn Lys Asp
            115                 120                 125
Gly Ile Ile Trp Val Ala Thr Glu Gly Ala Leu Asn Thr Pro Lys Asp
        130                 135                 140
His Ile Gly Thr Arg Asn Pro Ala Asn Asn Ala Ala Ile Val Leu Gln
145                 150                 155                 160
Leu Pro Gln Gly Thr Thr Leu Pro Lys Gly Phe Tyr Ala Glu Gly Ser
                165                 170                 175
Arg Gly Gly Ser Gln Ala Ser Ser Arg Ser Ser Ser Arg Ser Arg Asn
                180                 185                 190
Ser Ser Arg Asn Ser Thr Pro Gly Ser Ser Arg Gly Thr Ser Pro Ala
            195                 200                 205
Arg Met Ala Gly Asn Gly Gly Asp Ala Ala Leu Ala Leu Leu Leu Leu
        210                 215                 220
Asp Arg Leu Asn Gln Leu Glu Ser Lys Met Ser Gly Lys Gly Gln Gln
225                 230                 235                 240
Gln Gln Gly Gln Thr Val Thr Lys Lys Ser Ala Ala Glu Ala Ser Lys
                245                 250                 255
Lys Pro Arg Gln Lys Arg Thr Ala Thr Lys Ala Tyr Asn Val Thr Gln
                260                 265                 270
Ala Phe Gly Arg Arg Gly Pro Glu Gln Thr Gln Gly Asn Phe Gly Asp
            275                 280                 285
```

Gln Glu Leu Ile Arg Gln Gly Thr Asp Tyr Lys His Trp Pro Gln Ile
            290                 295                 300

Ala Gln Phe Ala Pro Ser Ala Ser Ala Phe Phe Gly Met Ser Arg Ile
305                 310                 315                 320

Gly Met Glu Val Thr Pro Ser Gly Thr Trp Leu Thr Tyr Thr Gly Ala
                325                 330                 335

Ile Lys Leu Asp Asp Lys Asp Pro Asn Phe Lys Asp Gln Val Ile Leu
                340                 345                 350

Leu Asn Lys His Ile Asp Ala Tyr Lys Thr Phe Pro Pro Thr Glu Pro
            355                 360                 365

Lys Lys Asp Lys Lys Lys Ala Asp Glu Thr Gln Ala Leu Pro Gln
370                 375                 380

Arg Gln Lys Lys Gln Gln Thr Val Thr Leu Leu Pro Ala Ala Asp Leu
385                 390                 395                 400

Asp Asp Phe Ser Lys Gln Leu Gln Gln Ser Met Ser Ser Ala Asp Ser
                405                 410                 415

Thr Gln Ala

<210> SEQ ID NO 3
<211> LENGTH: 344
<212> TYPE: PRT
<213> ORGANISM: Artificial sequence
<220> FEATURE:
<223> OTHER INFORMATION: recombinant spike protein S1

<400> SEQUENCE: 3

Val Ser Gly Thr Asn Gly Thr Lys Arg Phe Asp Asn Pro Val Leu Pro
1               5                   10                  15

Pro Pro Ala Ser Thr Glu Lys Ser Asn Ile Ile Pro Pro Gly Thr
                20                  25                  30

Thr Leu Asp Ser Lys Thr Gln Pro Pro Pro Tyr His Lys Asn Asn Lys
        35                  40                  45

Ser Trp Met Glu Pro Pro Pro Leu Lys Tyr Asn Glu Asn Gly Thr Ile
    50                  55                  60

Thr Pro Pro Pro Ala Trp Asn Arg Lys Arg Ile Ser Asn Cys Pro Pro
65                  70                  75                  80

Pro Ala Pro Gly Gln Thr Gly Lys Ile Ala Asp Tyr Asn Tyr Lys Leu
                85                  90                  95

Pro Asp Asp Phe Thr Pro Pro Pro Leu Phe Arg Lys Ser Asn Leu Lys
            100                 105                 110

Pro Phe Glu Arg Asp Ile Ser Thr Pro Pro Pro Val Cys Gly Pro Lys
        115                 120                 125

Lys Ser Thr Asn Leu Val Lys Asn Lys Cys Val Asn Pro Pro Pro Thr
    130                 135                 140

Glu Ser Asn Lys Lys Phe Leu Pro Phe Gln Gln Phe Gly Arg Asp Ile
145                 150                 155                 160

Ala Asp Thr Thr Asp Ala Val Arg Asp Pro Gln Thr Leu Pro Pro Pro
                165                 170                 175

Gln Thr Gln Thr Asn Ser Pro Arg Arg Ala Arg Ser Val Ala Pro Pro
            180                 185                 190

Pro Ile Ala Val Glu Gln Asp Lys Asn Thr Gln Glu Pro Pro Pro Ile
        195                 200                 205

Leu Pro Asp Pro Ser Lys Pro Ser Lys Arg Ser Phe Ile Pro Pro Pro
    210                 215                 220

```
Leu Gly Gln Ser Lys Arg Val Asp Phe Cys Gly Lys Pro Pro Pro Val
225                 230                 235                 240

Pro Ala Gln Glu Lys Asn Phe Thr Thr Ala Pro Pro Val Thr Gln
                245                 250                 255

Arg Asn Phe Tyr Glu Pro Pro Tyr Asp Pro Leu Gln Pro Glu Leu
            260                 265                 270

Asp Ser Phe Lys Glu Glu Leu Asp Lys Tyr Phe Lys Asn His Thr Ser
        275                 280                 285

Pro Asx Val Asp Leu Gly Asp Pro Pro Ala Lys Asn Leu Asn Glu
        290                 295                 300

Ser Leu Ile Asp Leu Gln Glu Leu Gly Lys Tyr Glu Gln Tyr Ile Pro
305                 310                 315                 320

Pro Pro Lys Phe Asp Glu Asp Ser Glu Pro Val Leu Lys Gly Val
                325                 330                 335

Lys Leu His Tyr Thr Lys Lys Lys
                340

<210> SEQ ID NO 4
<211> LENGTH: 1273
<212> TYPE: PRT
<213> ORGANISM: Artificial sequence
<220> FEATURE:
<223> OTHER INFORMATION: original spike protein S1

<400> SEQUENCE: 4

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
                20                  25                  30

Thr Arg Gly Val Tyr Tyr Pro Asp Lys Val Phe Arg Ser Ser Val Leu
            35                  40                  45

His Ser Thr Gln Asp Leu Phe Leu Pro Phe Phe Ser Asn Val Thr Trp
        50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240
```

```
Leu Leu Ala Leu His Arg Ser Tyr Leu Thr Pro Gly Asp Ser Ser
            245                 250                 255

Gly Trp Thr Ala Gly Ala Ala Tyr Val Gly Tyr Leu Gln Pro
            260                 265                 270

Arg Thr Phe Leu Leu Lys Tyr Asn Glu Asn Gly Thr Ile Thr Asp Ala
            275                 280                 285

Val Asp Cys Ala Leu Asp Pro Leu Ser Glu Thr Lys Cys Thr Leu Lys
        290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
        370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
            485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
        530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Gly Val Asn Cys Thr Glu Val Pro Val Ala Ile
        610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
```

```
                660             665             670
Ser Tyr Gln Thr Gln Thr Asn Ser Pro Arg Arg Ala Arg Ser Val Ala
            675             680             685

Ser Gln Ser Ile Ile Ala Tyr Thr Met Ser Leu Gly Ala Glu Asn Ser
        690             695             700

Val Ala Tyr Ser Asn Asn Ser Ile Ala Ile Pro Thr Asn Phe Thr Ile
705             710             715             720

Ser Val Thr Thr Glu Ile Leu Pro Val Ser Met Thr Lys Thr Ser Val
                725             730             735

Asp Cys Thr Met Tyr Ile Cys Gly Asp Ser Thr Glu Cys Ser Asn Leu
            740             745             750

Leu Leu Gln Tyr Gly Ser Phe Cys Thr Gln Leu Asn Arg Ala Leu Thr
        755             760             765

Gly Ile Ala Val Glu Gln Asp Lys Asn Thr Gln Glu Val Phe Ala Gln
    770             775             780

Val Lys Gln Ile Tyr Lys Thr Pro Pro Ile Lys Asp Phe Gly Gly Phe
785             790             795             800

Asn Phe Ser Gln Ile Leu Pro Asp Pro Ser Lys Pro Ser Lys Arg Ser
                805             810             815

Phe Ile Glu Asp Leu Leu Phe Asn Lys Val Thr Leu Ala Asp Ala Gly
            820             825             830

Phe Ile Lys Gln Tyr Gly Asp Cys Leu Gly Asp Ile Ala Ala Arg Asp
        835             840             845

Leu Ile Cys Ala Gln Lys Phe Asn Gly Leu Thr Val Leu Pro Pro Leu
    850             855             860

Leu Thr Asp Glu Met Ile Ala Gln Tyr Thr Ser Ala Leu Leu Ala Gly
865             870             875             880

Thr Ile Thr Ser Gly Trp Thr Phe Gly Ala Gly Ala Ala Leu Gln Ile
                885             890             895

Pro Phe Ala Met Gln Met Ala Tyr Arg Phe Asn Gly Ile Gly Val Thr
            900             905             910

Gln Asn Val Leu Tyr Glu Asn Gln Lys Leu Ile Ala Asn Gln Phe Asn
        915             920             925

Ser Ala Ile Gly Lys Ile Gln Asp Ser Leu Ser Ser Thr Ala Ser Ala
    930             935             940

Leu Gly Lys Leu Gln Asp Val Val Asn Gln Asn Ala Gln Ala Leu Asn
945             950             955             960

Thr Leu Val Lys Gln Leu Ser Ser Asn Phe Gly Ala Ile Ser Ser Val
                965             970             975

Leu Asn Asp Ile Leu Ser Arg Leu Asp Lys Val Glu Ala Glu Val Gln
            980             985             990

Ile Asp Arg Leu Ile Thr Gly Arg Leu Gln Ser Leu Gln Thr Tyr Val
        995             1000            1005

Thr Gln Gln Leu Ile Arg Ala Ala Glu Ile Arg Ala Ser Ala Asn
    1010            1015            1020

Leu Ala Ala Thr Lys Met Ser Glu Cys Val Leu Gly Gln Ser Lys
    1025            1030            1035

Arg Val Asp Phe Cys Gly Lys Gly Tyr His Leu Met Ser Phe Pro
    1040            1045            1050

Gln Ser Ala Pro His Gly Val Val Phe Leu His Val Thr Tyr Val
    1055            1060            1065

Pro Ala Gln Glu Lys Asn Phe Thr Thr Ala Pro Ala Ile Cys His
    1070            1075            1080
```

-continued

```
Asp Gly Lys Ala His Phe Pro Arg Glu Gly Val Phe Val Ser Asn
    1085                1090            1095
Gly Thr His Trp Phe Val Thr Gln Arg Asn Phe Tyr Glu Pro Gln
    1100                1105            1110
Ile Ile Thr Thr Asp Asn Thr Phe Val Ser Gly Asn Cys Asp Val
    1115                1120            1125
Val Ile Gly Ile Val Asn Asn Thr Val Tyr Asp Pro Leu Gln Pro
    1130                1135            1140
Glu Leu Asp Ser Phe Lys Glu Glu Leu Asp Lys Tyr Phe Lys Asn
    1145                1150            1155
His Thr Ser Pro Asp Val Asp Leu Gly Asp Ile Ser Gly Ile Asn
    1160                1165            1170
Ala Ser Val Val Asn Ile Gln Lys Glu Ile Asp Arg Leu Asn Glu
    1175                1180            1185
Val Ala Lys Asn Leu Asn Glu Ser Leu Ile Asp Leu Gln Glu Leu
    1190                1195            1200
Gly Lys Tyr Glu Gln Tyr Ile Lys Trp Pro Trp Tyr Ile Trp Leu
    1205                1210            1215
Gly Phe Ile Ala Gly Leu Ile Ala Ile Val Met Val Thr Ile Met
    1220                1225            1230
Leu Cys Cys Met Thr Ser Cys Cys Ser Cys Leu Lys Gly Cys Cys
    1235                1240            1245
Ser Cys Gly Ser Cys Cys Lys Phe Asp Glu Asp Asp Ser Glu Pro
    1250                1255            1260
Val Leu Lys Gly Val Lys Leu His Tyr Thr
    1265                1270
```

CORONAVIRUS ANTIBODY DETECTION KIT BASED ON MAGNETIC PARTICLE CHEMILUMINESCENCE

RELATED APPLICATIONS

This application is a national stage filing under 35 U.S.C. 371 of International Application No. PCT/CN2021/082727, filed Mar. 24, 2021, which claims priority to Chinese Application No. 202011432236.4, filed Dec. 10, 2020. The entire teachings of said application is incorporated by reference herein. International Application PCT/CN2021/082727 was published under PCT Article 21(2) in Chinese.

TECHNICAL FIELD

The present application belongs to the technical field of immunoassay detection, and relates to a novel coronavirus antibody detection kit based on magnetic particle chemiluminescence.

BACKGROUND

Coronaviruses are enveloped positive-sense single-stranded RNA viruses which are approximately 60-220 nm in diameter and widely found in humans and other mammals. Most coronaviruses cause mild infections, although two types of coronaviruses outbreak have raged and caused serious consequences: Severe Acute Respiratory Syndrome (SARS-CoV) and Middle East Respiratory Syndrome Coronavirus (MERS-CoV).

Novel coronavirus (2019-nCoV) may be transmitted through respiratory droplets, contacts, etc., and has strong human-to-human transmission capacity with a basic reproduction number R0 of about 2.2 (90% high-density interval 1.4-3.8). The most common symptoms of this virus infection are fever, cough, myalgia, or fatigue, and all patients are complicated by pneumonia, and chest CT examination reveals abnormalities. Some patients develop difficulty breathing after a week. The disease progresses rapidly in severe cases. Acute respiratory distress syndrome, septic shock, difficult-to-correct metabolic acidosis, and coagulation dysfunction may occur within a few days. In general, the novel coronavirus causes severe respiratory diseases.

At present, methods for diagnosing novel coronavirus pneumonia mainly include imaging diagnosis, molecular diagnosis, and serological diagnosis that includes colloidal gold, enzyme-linked immunosorbent assay and chemiluminescence. However, the imaging diagnosis has problems of different diseases with the same image, low specificity and is prone to lead to false-positive results. The molecular diagnosis, although has high specificity, shows low sensitivity and is prone to lead to false-negative results. For serological diagnosis, the colloidal gold is highly sensitive but has low specificity and is prone to lead to false-positive results; and the enzyme-linked immunosorbent assay requires manual operation, which has biological safety risks.

Therefore, it is important for the detection and diagnosis of novel coronavirus to provide a detection kit with high detection accuracy, good specificity and reduced biosafety risks by utilizing chemiluminescence.

SUMMARY

The present application provides a novel coronavirus antibody detection kit based on magnetic particle chemiluminescence, and also provides methods of preparation and use of the detection kit.

In the first aspect, the present application provides a novel coronavirus antibody detection kit based on magnetic particle chemiluminescence, including: a streptavidin magnetic particle, biotin-labeled novel coronavirus antigens, an acridine sulfonamide-labeled secondary antibody, a sample diluent and a quality control material; wherein the biotin-labeled novel coronavirus antigens include a recombinant nucleocapsid protein and a recombinant spike protein S1;

in the recombinant nucleocapsid protein, oligoproline residues are used to connect dominant epitopes of an original nucleocapsid protein, and oligolysine residues are used to form a C-terminus;

in the recombinant spike protein S1, oligoproline residues are used to connect dominant epitopes of an original spike protein S1, and oligolysine residues are used to form the C-terminus.

In the present application, the detection kit is based on a detection principle that is the chemiluminescence of streptavidin magnetic particles. When the sample to be tested, the biotin-labeled antigens and the streptavidin magnetic particles are mixed, incubated and washed, and then the signal substance-labeled secondary antibody is added, and incubated and washed again, a complex of magnetic particle-streptavidin-biotin-antigen-novel coronavirus IgM antibody-secondary antibody would be formed when a novel coronavirus IgM antibody in present in the sample. The luminous intensity value of the sample to be tested may be read through the signal substance labeled on the secondary antibody. The signal substance may be acridine ester, acridine sulfonamide, alkaline phosphatase and horseradish peroxidase, and preferably acridine sulfonamide in the present application.

In the present application, oligoproline residues -(P)n- are used to connect these dominant epitopes to form a recombinant antigen which has tandem-arranged predictive dominant epitopes and is easy to stretch and bend. This is conducive to the binding of antibodies to the dominant epitopes and improves detection sensitivity.

Oligolysine residues -(K)n- are used to form a C-terminus. Lysine residue has an extra amino group which is convenient to couple with labels such as biotin, acridinium ester, and carboxyl magnetic particles. In an aspect, it can increase the binding probability of the recombinant antigen to the label, and when the recombinant antigen binds to a solid-phase carrier through the C-terminal oligolysine residues, the N-terminal epitopes are easier to contact with an antibody. In another aspect, it can reduce the binding probability of dominant epitopes in the recombinant antigen to the label, and prevent the epitopes from being blocked by the label, which causes difficulty in antibody recognition.

In the present application, the detection kit can detect novel coronavirus IgM and IgG antibodies. The type of secondary antibody may be adjusted according to the type of antibody to be detected. For example, a goat anti-human IgM antibody may be selected as the secondary antibody when IgM is detected, and a goat anti-human IgG antibody may be selected as the secondary antibody when IgG is detected.

At the same time, the present application chooses to label the antigen with biotin, label the secondary antibody with acridine sulfonamide, and use an indirect manner for detection instead of a capture manner (the capture manner is to: label the secondary antibody with biotin, and label the antigen with acridine sulfonamide). This indirect manner can improve the accuracy of the detection result of the obtained kit.

In the present application, the mass ratio of the nucleocapsid protein and the spike protein S1 is set to (1 to 3):1, and most preferably 1.5:1. Compared with nucleocapsid or spike protein S1 alone, or other mixing ratios, such as a 4:1, 2:3, or 1:4, nucleocapsid protein and spike protein S1 with a ratio of 3:2 achieve higher discrimination degree between samples.

As a preferred technical solution of the present application, in the biotin-labeled novel coronavirus antigen, the mass ratio of activated biotin (Sulfo-NHS-LC-Biotin) to the novel coronavirus antigen is (0.06 to 0.48):1; for example, it may be 0.06:1, 0.1:1, 0.12:1, 0.15:1, 0.2:1, 0.25:1, 0.3:1, 0.4:1, 0.48:1, etc., preferably 0.24:1.

During the preparation process, novel coronavirus nucleocapsid protein and spike protein S1 are placed in a glassware, and diluted with 0.02 M PBS buffer; 12 μL of 10 mg/mL Sulfo-NHS-LC-Biotin solution is added to the above buffer solution of antigens, mixed well, and placed at room temperature for 2 hours in the dark; and dialyzed against 0.02 M PBS buffer at 2 to 8° C. overnight to obtain a stock solution of biotin-labeled antigens. Compared with samples added with 3, 6 and 24 μL, the sample added with 12 μL has a higher screening discrimination degree.

Preferably, the recombinant nucleocapsid protein includes the amino acid sequence as shown in SEQ ID NO: 1.

```
SEQ ID NO: 1 is:
GGPSDSTGSNQNGERSGARSKQRRPQGLPNNTPPPALNTPKDHIGTRN

PANNPPPGFYAEGSRGGSQASSRSSSRSRNSSRNSTPGSSRGTSPARM

AGNGGDPPPLESKMSGKGQQQQGQTVTKKSAAEASKKPRQKRTATKPP

PAFGRRGPEQTQGNFGDQELIRQGTDYKHWPPPKLDDKDPNFKDQPPP

TFPPTEPKKDKKKKADETQALPQRQKKQQTVPPPLDDFSKQLQQSMSS

ADSTQAKKK;
``` wherein, all underlined are dominant epitopes of recombinant nucleocapsid protein.

The sequence of the original nucleocapsid protein is as shown in SEQ ID NO: 2:

```
MSDNGPQNQRNAPRITFGGPSDSTGSNQNGERSGARSKQRRPQGLPNN

TASWFTALTQHGKEDLKFPRGQGVPINTNSSPDDQIGYYRRATRRIRG

GDGKMKDLSPRWYFYYLGTGPEAGLPYGANKDGIIWVATEGALNTPKD

HIGTRNPANNAAIVLQLPQGTTLPKGFYAEGSRGGSQASSRSSSRSRN

SSRNSTPGSSRGTSPARMAGNGGDAALALLLLDRLNQLESKMSGKGQQ

QQGQTVTKKSAAEASKKPRQKRTATKAYNVTQAFGRRGPEQTQGNFGD

QELIRQGTDYKHWPQIAQFAPSASAFFGMSRIGMEVTPSGTWLTYTGA

IKLDDKDPNFKDQVILLNKHIDAYKTFPPTEPKKDKKKKADETQALPQ

RQKKQQTVTLLPAADLDDFSKQLQQSMSSADSTQA.
```

The original sequence has been analyzed with DNAStar Protean software. Amino acid sequences 18 to 49, 138 to 154, 170 to 216, 230 to 266, 273 to 301, 338 to 349, 362 to 392, and 400 to 419 are predicted to be dominant epitopes as they are mostly located in the beta-turn (mostly located on the surface of the protein, being easy to bind to an antibody), and have high hydropathy index, antigenic index, and surface accessibility.

In the present application, different dominant epitopes may also be randomly arranged and combined to form a new recombinant antigen. Since dominant epitopes are still remained, its effect is similar to the amino acid sequence as shown in SEQ ID NO: 1.

Preferably, benzene ring-containing amino acid residues (such as phenylalanine F/tryptophan W/tyrosine Y) are attached to both ends of the recombinant nucleocapsid protein, which is beneficial to improve the stability of the recombinant antigen.

Preferably, the recombinant spike protein S1 includes the amino acid sequence as shown in SEQ ID NO: 3.

```
SEQ ID NO: 3 is:
VSGTNGTKRFDNPVLPPPASTEKSNIIPPPGTTLDSKTQPPPYHKNNK

SWMEPPPLKYNENGTITPPPAWNRKRISNCPPPAPGQTGKIADYNYKL

PDDFTPPPLFRKSNLKPFERDISTPPPVCGPKKSTNLVKNKCVNPPPT

ESNKKFLPFQQFGRDIADTTDAVRDPQTLPPPQTQTNSPRRARSVAPP

PIAVEQDKNTQEPPPILPDPSKPSKRSFIPPPLGQSKRVDFCGKPPPV

PAQEKNFTTAPPPVTQRNFYEPPPYDPLQPELDSFKEELDKYFKNHTS

PBVDLGDPPPAKNLNESLIDLQELGKYEQYIPPPKFDEDDSEPVLKGV

KLHYTKKK;
``` wherein, all underlined are dominant epitopes of recombinant spike protein S1.

The sequence of the original spike protein S1 is as shown in SEQ ID NO: 4:

```
MFVFLVLLPLVSSQCVNLTTRTQLPPAYTNSFTRGVYYPDKVFRSSVL

HSTQDLFLPFFSNVTWFHAIHVSGTNGTKRFDNPVLPFNDGVYFASTE

KSNIIRGWIFGTTLDSKTQSLLIVNNATNVVIKVCEFQFCNDPFLGVY

YHKNNKSWMESEFRVYSSANNCTFEYVSQPFLMDLEGKQGNFKNLREF

VFKNIDGYFKIYSKHTPINLVRDLPQGFSALEPLVDLPIGINITRFQT

LLALHRSYLTPGDSSSGWTAGAAAYYVGYLQPRTFLLKYNENGTITDA

VDCALDPLSETKCTLKSFTVEKGIYQTSNFRVQPTESIVRFPNITNLC

PFGEVFNATRFASVYAWNRKRISNCVADYSVLYNSASFSTFKCYGVSP

TKLNDLCFTNVYADSFVIRGDEVRQIAPGQTGKIADYNYKLPDDFTGC

VIAWNSNNLDSKVGGNYNYLYRLFRKSNLKPFERDISTEIYQAGSTPC

NGVEGFNCYFPLQSYGFQPTNGVGYQPYRVVVLSFELLHAPATVCGPK

KSTNLVKNKCVNFNFNGLTGTGVLTESNKKFLPFQQFGRDIADTTDAV

RDPQTLEILDITPCSFGGVSVITPGTNTSNQVAVLYQGVNCTEVPVAI

HADQLTPTWRVYSTGSNVFQTRAGCLIGAEHVNNSYECDIPIGAGICA

SYQTQTNSPRRARSVASQSIIAYTMSLGAENSVAYSNNSIAIPTNFTI

SVTTEILPVSMTKTSVDCTMYICGDSTECSNLLLQYGSFCTQLNRALT

GIAVEQDKNTQEVFAQVKQIYKTPPIKDFGGFNFSQILPDPSKPSKRS

FIEDLLFNKVTLADAGFIKQYGDCLGDIAARDLICAQKFNGLTVLPPL

LTDEMIAQYTSALLAGTITSGWTFGAGAALQIPFAMQMAYRFNGIGVT

QNVLYENQKLIANQFNSAIGKIQDSLSSTASALGKLQDVVNQNAQALN
```

-continued

```
TLVKQLSSNFGAISSVLNDILSRLDKVEAEVQIDRLITGRLQSLQTYV

TQQLIRAAEIRASANLAATKMSECVLGQSKRVDFCGKGYHLMSFPQSA

PHGVVFLHVTYVPAQEKNFTTAPAICHDGKAHFPREGVFVSNGTHWFV

TQRNFYEPQIITTDNTFVSGNCDVVIGIVNNTVYDPLQPELDSFKEEL

DKYFKNHTSPDVDLGDISGINASVVNIQKEIDRLNEVAKNLNESLIDL

QELGKYEQYIKWPWYIWLGFIAGLIAIVMVTIMLCCMTSCCSCLKGCC

SCGSCCKFDEDDSEPVLKGVKLHYT.
```

The original sequence has been analyzed with DNAStar Protean software. Amino acid sequences 70 to 84, 93 to 101, 107 to 115, 145 to 154, 277 to 286, 352 to 361, 410 to 430, 455 to 470, 524 to 540, 553 to 582, 675 to 688, 770 to 780, 805 to 818, 1034 to 1045, 1068 to 1078, 1104 to 1111, 1138 to 1168, 1180 to 1210, and 1255 to 1273 are predicted to be dominant epitopes as they are mostly located in the beta-turn (mostly located on the surface of the protein, being easy to bind to an antibody), and have high hydropathy index, antigenic index, and surface accessibility.

In the present application, different dominant epitopes may also be randomly arranged and combined to form a new recombinant antigen. Since dominant epitopes are still remained, its effect is similar to the amino acid sequence shown in SEQ ID NO: 3.

Preferably, benzene ring-containing amino acid residues (such as phenylalanine F/tryptophan W/tyrosine Y) are attached to both ends of the recombinant nucleocapsid protein, which is beneficial to improve the stability of the recombinant antigen.

Preferably, the biotin-labeled novel coronavirus antigens are dispersed in PBS buffer.

Preferably, the concentration of the PBS buffer is 0.02 to 0.1 M, for example, it may be 0.02 M, 0.05 M, 0.06 M, 0.08 M, 0.1 M, etc., preferably 0.02 M.

Preferably, the pH of the PBS buffer is 7.2 to 9.0, for example, it may be 7.2, 7.3, 7.5, 7.6, 7.8, 8.0, 8.2, 8.5, 8.8 or 9.0, etc., preferably 7.2.

In the present application, the buffer system is 0.02 M PBS (pH 7.2) buffer, which has the best effect compared to 0.1 M PBS (pH 7.2), 0.05 M PBS (pH 7.2), 0.1 M CBS (pH 9.0), 0.05 M CBS (pH 9.0) or 0.02 M CBS (pH 9.0) buffer.

As a preferred technical solution of the present application, the acridine sulfonamide-labeled secondary antibody is dispersed in a CBS buffer.

Preferably, the concentration of the CBS buffer is 0.02 to 0.1 M, for example, it may be 0.02 M, 0.05 M, 0.06 M, 0.08 M or 0.1 M, etc., preferably 0.1 M.

Preferably, the pH of the CBS buffer is 7.2 to 9.0, for example, it may be 7.2, 7.3, 7.5, 7.6, 7.8, 8.0, 8.2, 8.5, 8.8 or 9.0, etc., preferably 9.0.

In the present application, the buffer system is 0.1 M CBS (pH 9.0) buffer, which has the best effect compared to 0.1 M PBS (pH 7.2), 0.05 M PBS (pH 7.2), 0.02 M PBS (pH 7.2), 0.1 M CBS (pH 9.0), 0.05 M CBS (pH 9.0) or 0.02 M CBS (pH 9.0) buffer.

As a preferred technical solution of the present application, the sample diluent contains any one or a combination of at least two of bovine serum albumin, a rheumatoid factor adsorbent, a bacteriostatic agent, urea or a blocking agent.

By using a blocking agent, the interference of heterophilic antibodies in blood samples can be eliminated; by using a rheumatoid factor adsorbent, the interference of rheumatoid factors in blood samples can be eliminated; and by using urea, the non-specific binding of the blood sample to the solid phase carrier can be reduced.

In the present application, the sample diluent may be 0.01 M PBS, and added with by a mass fraction of 0.4 to 0.6% (for example, it may be 0.42%, 0.44%, 0.45%, 0.48%, 0.5%, 0.55%, 0.58% or 0.6%, etc.), a bacteriostatic agent ProClin300 by a mass fraction of 0.01 to 0.05% (for example, it may be 0.012%, 0.015%, 0.02%, 0.025%, 0.03%, 0.035%, 0.04% or 0.05%, etc.), urea by a mass fraction of 1 to 10% (for example, it may be 1%, 2%, 3%, 5%, 6%, 8% or 10%, etc.) and a blocking agent by a mass fraction of 0.1 to 0.5% (for example, it may be 0.12%, 0.15%, 0.2%, 0.25%, 0.3%, 0.35%, 0.4% or 0.5%, etc.).

As a preferred technical solution of the present application, the quality control material includes a positive quality control material and a negative quality control material.

In a preferred embodiment, the positive quality control material is a buffer containing a novel coronavirus antibody.

As a preferred technical solution of the present application, the novel coronavirus antibody detection kit further includes an excitation solution and a washing solution.

In a second aspect, the present application provides a method for preparing the novel coronavirus antibody detection kit as described in the first aspect, comprising the following steps:

(1) preparing biotin-labeled novel coronavirus antigens: mixing the nucleocapsid protein and spike protein S1 of the novel coronavirus as antigens with a PBS buffer, adding activated biotin and labeling for 1.5 to 2.5 hours, and then dialyzing to obtain the biotin-labeled novel coronavirus antigens;

(2) preparing an acridine sulfonamide-labeled secondary antibody: mixing a secondary antibody with a CBS buffer, adding NSP-SA-NHS and labeling for 0.5 to 1.5 h, adding a lysine solution, and dialyzing to obtain the acridine sulfonamide-labeled secondary antibody; and (3) packaging the biotin-labeled novel coronavirus antigens, the acridine sulfonamide-labeled secondary antibody, a streptavidin magnetic particle, a sample diluent and a quality control material, separately, to obtain the novel coronavirus antibody detection kit.

In a third aspect, the present application also provides a method for using the novel coronavirus antibody detection kit as described in the first aspect, comprising the following steps:

adding the biotin-labeled novel coronavirus antigens and streptavidin magnetic particles to a sample to be tested, performing a first incubation, washing, then adding the acridine sulfonamide-labeled secondary antibody, performing a second incubation, washing, and then detecting to obtain detected results.

In the present application, a two-step method is used to detect the sample to be tested, that is, the sample, biotin-labeled antigens and streptavidin magnetic particles are mixed and incubated, and then the acridine sulfonamide-labeled antibody is added and incubated. Compared with a three-step method (where streptavidin magnetic particles and biotin-labeled antigens are mixed and incubated, then the sample is added and incubated, and the acridine sulfonamide-labeled antibody is added and incubated) and a one-step method (where the sample, biotin-labeled antigens, streptavidin magnetic particles and acridine sulfonamide-labeled antibody are directly mixed and incubated), the two-step method shows better detection results.

Preferably, the sample to be tested is serum or plasma. The absolute value of the relative deviation of the detected luminescence value between different sample types (plasma/ serum) of a same sample is less than 10%. The detected results for plasma and serum are considered to be the same.

Preferably, the sample to be tested is diluted with a sample diluent. When a sample is diluted by 25 times, 50 times, 100 times, 200 times, 400 times respectively with a sample diluent, and detected using a chemiluminescence method, it shows that a highest discrimination degree is achieved when the sample dilution factor is 100 times.

Preferably, the titer ratio of the sample to be tested after dilution is 1:(103 to 110), for example, it may be 1:103, 1:104, 1:105, 1:106, 1:107, 1:108, 1:109 or 1:110, etc., preferably 1:103.

In the present application, the optimal reaction conditions for detection are that the addition volume of the sample is 50, 75, and 100 μL, the addition volume of the biotin-labeled antigens is 25, 50, and 75 μL, the addition volume of the magnetic particles is 30, 40, and 50 μL, the first step is reacted for 4, 6, 8, 10 min, the optimal concentration of the acridine sulfonamide-labeled secondary antibody is 1, 0.5, 0.25, 0.125 μg/mL, the second step is reacted for 4, 6, 8, 10 min, and the washing is carried out for 1, 2, 3, 4 times, respectively.

Preferably, the volume ratio of the sample to be tested, the biotin-labeled novel coronavirus antigens and streptavidin magnetic particles is (50 to 100):(25 to 75):(30 to 50), for example, it may be 50:25:30, 75:25:30, 100:25:30, 50:50:30, 50:75:30, 50:75:40, 100:50:40, 100:50:50 or 100:75:50, etc., preferably 100:50:40.

Preferably, the working concentration of the acridine sulfonamide-labeled secondary antibody is 0.125 to 1 μg/mL, for example, it may be 0.125 μg/mL, 0.25 μg/mL, 0.5 μg/mL, 0.75 μg/mL, 0.8 μg/mL, 0.9 μg/mL, or 1 μg/mL, etc., preferably 0.25 μg/mL.

Preferably, the first incubation is carried out for 5 to 15 min, for example, 5 min, 6 min, 7 min, 8 min, 9 min, 10 min, 12 min, 14 min or 15 min, etc., preferably 8 min.

Preferably, the second incubation is carried out for 5 to 15 min, for example, 5 min, 6 min, 7 min, 8 min, 9 min, 10 min, 12 min, 14 min, or 15 min, etc., preferably 8 min.

In some specific embodiments, if the index I in the detected results is equal to or greater than 1.0, the sample to be tested is positive; if the index I in the detected results is less than 1.0, the sample to be tested is negative.

The range of values described in the present application includes not only the point values exemplified above, but also any point values between the above-mentioned range of values not exemplified above, and for reasons of space and brevity, the present application does not exhaust the specific point values included in the said range.

Compared with the existing art, the present application has beneficial effects described below.

(1) The novel coronavirus antibody detection kit based on chemiluminescence of magnetic particles provided in the present application selects streptavidin magnetic particles, label antigens with biotin, and label a secondary antibody with acridine sulfonamide. In an aspect, by adjusting the magnetic particle coupling and sealing conditions and adjusting the composition of the system stabilizer, the false positive factors in blood samples can be effectively reduced. In another aspect, by using the method of mixing two antigens of novel coronavirus (spike protein and nucleocapsid protein) at a mass ratio of recombinant nucleocapsid protein and spike protein S1 of (1 to 3):1, the specificity of detection is improved.

(2) The antibody detection kit provided in the present application uses recombinant nucleocapsid protein and recombinant spike protein as antigens of novel coronavirus. The recombinant proteins have dominant epitopes of the original protein sequences, and have high hydropathy index, antigenic index, and surface accessibility, thereby the sensitivity of detection is significantly improved.

(3) The detection kit provided by the present application has good sensitivity, with a lower limit of detection of 1:103, high precision, and high repeatability between multiple repeated tests, and good specificity. It gives negative detection results on samples that may cause cross-reactions and normal human samples. Moreover, as for substances that may cause interference in the samples, the relative deviation of the detection results is controlled. Moreover, through cooperated automatic detection equipment, it can effectively avoid operator exposure risk, improve biological safety, and can also achieve high-throughput detection and increase the speed of novel coronavirus detection.

DETAILED DESCRIPTION

Figure 1:
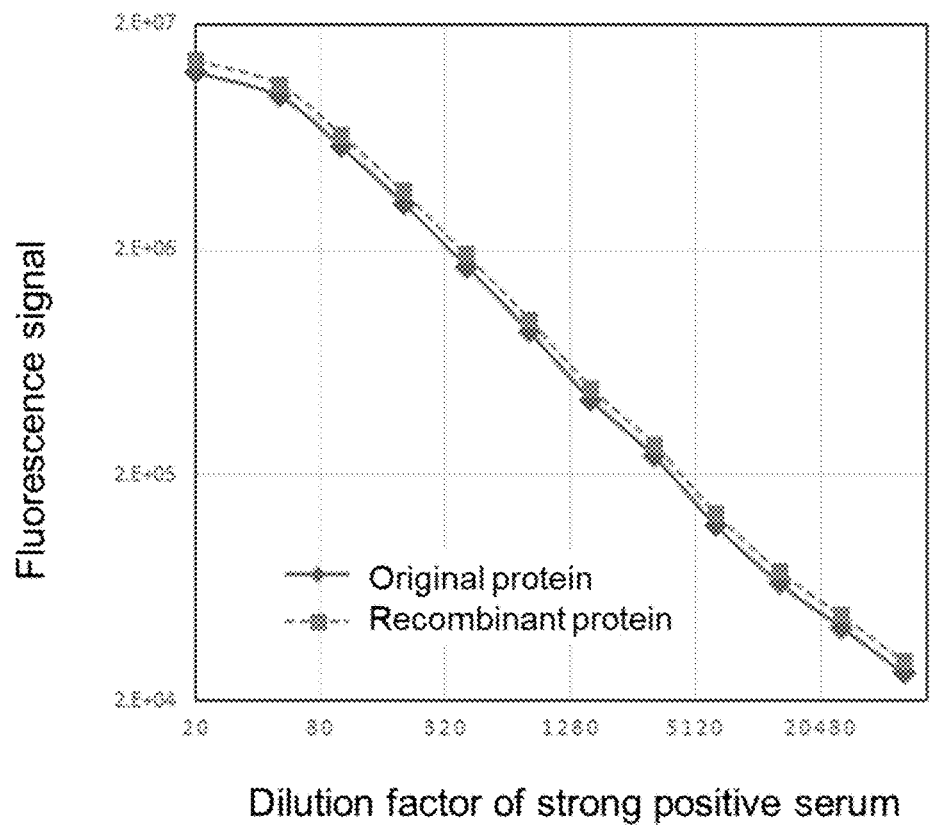
FIG. 1 is a graph showing the fluorescence detection results obtained in Test Example 1 where detection kits prepared with recombinant proteins and original proteins as antigens were used to detect strong positive serum with different dilution factor.

The technical solutions of the present application will be further explained below in conjunction with the drawings and specific implementations. However, the following examples are only simple examples of the present application, and do not represent or limit the protection scope of the present application. The protection scope of the present application is defined by the claims.

In the following examples, experiments and detections were carried out by using common technical means in the art, unless otherwise specified.

Example 1

This example provided a novel coronavirus IgM antibody detection kit based on magnetic particle chemiluminescence, specifically comprising:

0.3 mg/mL of streptavidin magnetic particles, biotin-labeled novel coronavirus antigens, an acridine sulfonamide-labeled goat anti-human IgM antibody, a sample diluent, a positive quality control material, a negative quality control material, a sample diluent and a washing solution.

(1) The preparation method of the biotin-labeled novel coronavirus antigen was as follows:

0.3 mg of recombinant nucleocapsid protein and 0.2 mg of recombinant spike protein S1 of the novel coronavirus were diluted with 0.02 M PBS (pH 7.2) buffer. The final concentration of the mixed antigens was 1 mg/mL.

The sequence of the recombinant nucleocapsid protein was SEQ ID NO: 1; and the sequence of the recombinant spike protein S1 was SEQ ID NO: 3.

12 μL of 10 mg/mL activated biotin was added to the above antigen buffer, mixed well, and kept at room temperature in the dark for 2 hours; and dialyzed against 0.02 M PBS buffer at 4° C. overnight to obtain a stock solution of the biotin-labeled antigens.

The working concentration of the biotin-labeled novel coronavirus antigens was 1 μg/mL.

(2) The preparation method of goat anti-human IgM antibody labeled with acridine sulfonamide was as follows:

0.2 mg of goat anti-human IgM antibody was placed in a glassware, and was diluted with 0.1 M CBS (pH 9.0) buffer to 1 mg/mL. 9.1 µL of 2 mg/mL NSP-SA-NHS solution was added to the above diluted antibody solution, mixed well, and kept at room temperature in the dark for 60 min.

Then 1.33 µL of 10% lysine solution was added, mixed well, and kept at room temperature in the dark for 30 minutes; and dialyzed against 0.02 M PBS buffer solution at 4° C. overnight to obtain a stock solution of the acridine sulfonamide-labeled antibody.

The working concentration of the acridine sulfonamide-labeled goat anti-human IgM antibody was 1 µg/mL.

Example 2

This example provided novel coronavirus IgM antibody detection kits based on magnetic particle chemiluminescence. The difference from Example 1 was that the mass ratios of recombinant nucleocapsid protein and recombinant spike protein S1 were set to 5:0, 4:1, 2:3, 1:4, and 0:5, respectively.

The degree of discrimination was tested, and the results are shown in Table 1.

TABLE 1

| Reference material | The ratio of nucleocapsid protein to spike protein S1 | | | | | |
| --- | --- | --- | --- | --- | --- | --- |
| | 5:0 | 4:1 | 3:2 | 2:3 | 1:4 | 0.5 |
| | S/C0 | | | | | |
| N01 | 0.18 | 0.18 | 0.18 | 0.17 | 0.18 | 0.19 |
| N02 | 0.28 | 0.28 | 0.28 | 0.25 | 0.28 | 0.29 |
| N03 | 0.32 | 0.32 | 0.31 | 0.30 | 0.33 | 0.32 |
| N04 | 0.34 | 0.37 | 0.35 | 0.33 | 0.36 | 0.36 |
| N05 | 0.35 | 0.36 | 0.36 | 0.36 | 0.38 | 0.37 |
| N06 | 0.42 | 0.44 | 0.41 | 0.71 | 1.10 | 1.40 |
| N07 | 0.42 | 0.40 | 0.42 | 0.41 | 0.42 | 0.43 |
| N08 | 0.39 | 0.38 | 0.38 | 0.36 | 0.38 | 0.36 |
| N09 | 0.27 | 0.25 | 0.26 | 0.26 | 0.27 | 0.25 |
| N10 | 2.08 | 1.16 | 0.37 | 0.27 | 0.21 | 0.12 |
| N11 | 0.16 | 0.23 | 0.18 | 0.20 | 0.18 | 0.07 |
| N12 | 0.09 | 0.11 | 0.09 | 0.09 | 0.09 | 0.08 |
| N13 | 1.51 | 0.74 | 0.21 | 0.18 | 0.16 | 0.10 |
| N14 | 0.34 | 0.42 | 0.34 | 0.33 | 0.31 | 0.35 |
| N15 | 0.10 | 0.11 | 0.10 | 0.10 | 0.09 | 0.10 |
| P01 | 26.69 | 25.31 | 26.77 | 24.13 | 25.45 | 28.19 |
| P02 | 11.51 | 11.91 | 11.42 | 12.09 | 12.15 | 13.14 |
| P03 | 8.44 | 9.68 | 8.92 | 8.78 | 8.39 | 8.80 |
| P04 | 5.55 | 5.27 | 5.20 | 5.68 | 5.98 | 5.74 |
| P05 | 3.45 | 3.42 | 3.36 | 3.41 | 3.38 | 3.43 |
| L1 | 0.44 | 0.43 | 0.43 | 0.44 | 0.43 | 0.38 |
| L2 | 1.00 | 1.00 | 1.00 | 1.00 | 1.00 | 1.00 |
| L3 | 5.05 | 4.59 | 4.59 | 5.21 | 4.66 | 4.78 |

The reference materials were standard samples, which were tested samples used in the development of the kit. They were numbered N01 to N15 (negative samples), P01 to 05 (positive samples) and L1 to L3 (quality control materials). As shown from the above table, the negative coincidence rate (i.e., a case where the discrimination degree was less than 1) was 14/15, when the ratios of nucleocapsid protein and spike protein S1 were 5:0, 4:1, 1:4, and 0:5.

Specifically: when the ratio was 5:0, the discrimination degree of sample N10 was 2.08; when the ratio was 4:1, the discrimination degree of sample N10 was 1.16; when the ratio was 1:4, the discrimination degree of sample N06 was 1.10; and when the ratio was 0:5, the discrimination degree of sample N06 was 1.40.

When the ratio of the two was 3:2 and 2:3, the negative coincidence rates were both 15/15, and the positive coincidence rates were both 5/5. When the ratio was 2:3, the detected value of the negative reference material N06 was 0.71, which was larger than the detected value of N06 when the ratio was 3:2, i.e., 0.41, and was close to the threshold value (for negative samples, the smaller the discrimination value, the better). Therefore, the ratio of 2:3 leaded to poor detection effect. For the sake of high specificity, the sample discrimination degree was better when 3:2 was selected. Therefore, the ratio of nucleocapsid protein and spike protein S1 was selected to be 3:2.

Example 3

This example provided novel coronavirus IgM antibody detection kits based on magnetic particle chemiluminescence. The difference from Example 1 was that the addition amounts of the Sulfo-NHS-LC-Biotin solution were set to 3 µL, 6 µL and 24 µL, respectively.

The specific results are shown in Table 2 below.

TABLE 2

| Sulfo-NHS-LC-Biotin dosage (µL) | 3 | 6 | 12 | 24 |
| --- | --- | --- | --- | --- |
| Sample | S/C0 | | | |
| N01 | 0.11 | 0.11 | 0.10 | 0.10 |
| P01 | 6.68 | 6.94 | 7.18 | 7.01 |
| P05 | 1.00 | 1.00 | 1.00 | 1.00 |

Example 4

This example provided novel coronavirus IgM antibody detection kits based on magnetic particle chemiluminescence. The difference from Example 1 was that the buffer systems of the biotin-labeled novel coronavirus antigen were set to 0.1 M PBS (pH 7.2), 0.05 M PBS (pH 7.2), 0.1 M CBS (pH 9.0), 0.05 M CBS (pH 9.0), and 0.02 M CBS (pH 9.0).

The specific results are shown in Table 3 below.

TABLE 3

| Sample | 0.1M PBS | 0.05M PBS | 0.02M PBS |
| --- | --- | --- | --- |
| | S/C0 | | |
| N01 | 0.11 | 0.11 | 0.10 |
| P01 | 6.26 | 6.89 | 7.06 |
| P05 | 1.00 | 1.00 | 1.00 |
| N01 | 0.10 | 0.10 | 0.10 |
| P01 | 6.49 | 6.13 | 6.26 |
| P05 | 1.00 | 1.00 | 1.00 |

Example 5

This example provided novel coronavirus IgM antibody detection kits based on magnetic particle chemiluminescence. The difference from Example 1 was that the buffer systems of the acridine sulfonamide-labeled secondary antibody were set to 0.1 M PBS (pH7.2), 0.05 M PBS (pH7.2), 0.02 M PBS (pH 7.2), 0.05 M CBS (pH 9.0), and 0.02 M CBS (pH 9.0).

The specific results are shown in Table 4 below.

TABLE 4

| Sample | 0.1M PBS | 0.05M PBS S/C0 | 0.02M PBS |
|---|---|---|---|
| N01 | 0.10 | 0.10 | 0.10 |
| P01 | 6.88 | 7.01 | 7.03 |
| P05 | 1.00 | 1.00 | 1.00 |
| N01 | 0.09 | 0.10 | 0.10 |
| P01 | 7.28 | 7.06 | 6.95 |
| P05 | 1.00 | 1.00 | 1.00 |

The tested samples in Examples 3, 4 and 5 were standard samples, which were tested samples used in the development of the kit, and were numbered N01, P01 and P05.

It can be seen from the experimental results that in Table 2, when the addition amount of Sulfo-NHS-LC-Biotin solution was 12 μL, the positive sample P01 had the highest discrimination degree; in Table 3, when the antigen buffer system was 0.02 M PBS, the positive sample P01 had the highest discrimination degree; and in Table 4, when the buffer system of the secondary antibody was 0.1 M CBS, the positive sample P01 had the highest discrimination degree. Therefore, when the conditions provided in Example 1 included an addition amount of Sulfo-NHS-LC-Biotin solution of 12 μL, an antigen buffer system of 0.02 M PBS, and a buffer system of the secondary antibody of 0.1 M CBS, the maximum discrimination degree was obtained.

Example 6

This example provided three different detection steps, specifically comprising:

(1) Three-step method: 50 μL of streptavidin magnetic particles were added to 50 μL of biotin-labeled antigens and incubated for 5 min, and washed. 100 μL of a reference material was added, incubated for 10 min, and washed. 50 μL of acridine sulfonamide labeled antibody was added, incubated for 10 min, and washed. Excitation solution was added to detect the luminescence value.

(2) Two-step method: 100 μL of a reference material was added with 50 μL of biotin-labeled antigens and 50 μL of streptavidin magnetic particles, incubated for 10 min, and washed.
50 μL of acridine sulfonamide-labeled antibody was added, incubated for 10 min, and washed. Excitation solution was added to detect the luminescence value.

(3) One-step method: 100 μL of a reference material was added with 50 μL of biotin-labeled antigens, 50 μL of acridine sulfonamide-labeled antibody, and 50 μL of streptavidin magnetic particles, incubated for 20 min, and washed. Excitation solution was added to detect the luminescence value.

Discrimination degree was tested, and the results are shown in Table 5.

TABLE 5

| Sample | Three-step method | Two-step method S/C0 | One-step method |
|---|---|---|---|
| N01 | 0.14 | 0.08 | 0.23 |
| P01 | 4.67 | 7.87 | 3.56 |
| P05 | 1.00 | 1.00 | 1.00 |

The reference materials were standard samples, which were tested samples used in the development of the kit, and numbered N01, P01 and P05. It can be seen from the above table that the two-step method achieved higher discrimination degree. Therefore, the two-step method was selected.

Test Example 1: Evaluation of the Lower Limit of Detection 3 positive plasmas were diluted by multiples to obtain samples whose detected results covered the threshold value. For each gradient, samples were diluted in triplicate, and each sample was tested 20 times with the kit used in Example 1 (For chemiluminescence detection, the sample needs to be diluted 100 times).

The positive detection rate of each sample was calculated, and the tested antibody titer level that resulted in a positive detection rate in the range of 90 to 95% was selected as the lower limit of detection.

The test results are shown in Table 6 below.

TABLE 6

| Dilution times of positive samples | Mean | | | Positive detection rate (%) | | |
|---|---|---|---|---|---|---|
| | 1 | 2 | 3 | 1 | 2 | 3 |
| Titer (1:105.6) | 1.09 | 1.09 | 1.10 | 98.33 | 100.00 | 96.67 |
| Titer (1:95) | 0.99 | 0.98 | 0.99 | 45.00 | 41.67 | 45.00 |
| Titer (1:86.4) | 0.94 | 0.93 | 0.93 | 16.67 | 15.00 | 8.33 |
| Titer (1:114.4) | 1.26 | 1.24 | 1.25 | 100.00 | 100.00 | 100.00 |
| Titer (1:103) | 1.07 | 1.07 | 1.07 | 95.00 | 93.33 | 93.33 |
| Titer (1:93.6) | 0.96 | 0.97 | 0.96 | 23.33 | 30.00 | 26.67 |
| Titer (1:123.3) | 1.29 | 1.29 | 1.29 | 100.00 | 100.00 | 100.00 |
| Titer (1:111) | 1.19 | 1.20 | 1.19 | 100.00 | 100.00 | 100.00 |
| Titer (1:100.9) | 1.02 | 1.03 | 1.02 | 66.67 | 70.00 | 66.67 |

When the titer of the serially diluted sample was 1:103, the positive detection rate was in the range of 90 to 95%. Thus, a titer of 1:103 was used as the lower limit of detection.

In addition, a strong positive sample was used as the tested sample, and detected with detection kits prepared using the recombinant protein and the original protein as the antigen. The fluorescence detection results obtained for the strongly positive serum diluted at different factors are shown in FIG. 1.

It can be seen from FIG. 1 that when the same titer was detected, the recombinant protein achieved significantly higher fluorescence intensity than that of the original protein. It shows that the recombinant protein provided by the present application has higher sensitivity in detection.

Test Example 2: Evaluation of Precision 4 clinical samples (1 negative sample, 1 marginal positive sample, 1 moderate positive sample, 1 strong positive sample) and 2 quality control materials were tested with 2 models, with 2 operators for each model, and a total of 4 operators, and 3 batches of the kit provided in Example 1 were used for each model. The detection was lasted for 5 days, and 5 replicates were performed for each sample per day (2 models×3 kit batches×5 days×5 replicates/day=150 results/sample).

Model 1: Automatic chemiluminescence analyzer from CHONGQING KEYSMILE BIOTECHNOLOGY Co., Ltd., model: SMART 6500;

Model 2: Automatic chemiluminescence immunoassay analyzer from CHONGQING KEYSMILE BIOTECHNOLOGY Co., Ltd., model: SMART 500S.

The test results are shown in Table 7 below.

TABLE 7

| Sample | SMART 6500 | | | | |
|---|---|---|---|---|---|
| | Test total mean | Repeatability | | Indoor precision | |
| | | SDR | % CV | $SD_{WI}$ | % CV |
| Positive quality control material | 4.74 | 0.05 | 0.96% | 0.05 | 1.10% |
| Moderate positive sample | 3.24 | 0.09 | 2.74% | 0.13 | 4.08% |
| Strong positive sample | 10.13 | 0.35 | 3.41% | 0.47 | 4.62% |

| Sample | Test total mean | Number of results with I value ≥ 1.0 | Number of results with I value < 1.0 |
|---|---|---|---|
| Marginal positive sample | 1.08 | 75 | 0 |
| Negative sample | 0.21 | 0 | 75 |
| Negative quality control material | 0.13 | 0 | 75 |

SDR represents the standard deviation due to random error; SDwi represents the standard deviation due to kit batches, daytime repeat assay, operators and random errors within a laboratory.

It can be seen from the data analysis results of the above table that, when detected by the model SMART 6500, the CVs of repeatability, indoor precision and inter-batch precision of the moderate positive sample, the strong positive sample and the positive quality control material were less than or equal to 10%, which met the requirements (repeatability CV<10%, inter-assay CV<15%); the positive detection rate of the marginal positive sample was ≥95% which met the requirements; and the negative detection rate of negative samples and negative controls should be 100%, which met the requirements;

Similarly, the test results of the model SMART 500S also met the requirements. For the sake of space and conciseness, it will not be listed here.

Test Example 3: Evaluation of Specificity

The novel coronavirus antibody detection kit provided by the present application was used to detect samples that may cause cross-reactions and normal human samples, and it was observed whether the detection result was positive. A positive result would indicate that such samples had an impact on the novel coronavirus IgM antibody detection.

Plasma samples of endemic human coronavirus (HKU1, OC43, NL63 and 229E) were confirmed by western blot and serological methods to contain specific IgM antibodies; H1N1 (novel A H1N1 influenza virus (2009), seasonal H1N1 influenza virus) IgM antibody-positive plasma samples.

The test results are shown in Table 8.

TABLE 8

| Number | Names of samples that may cross | Detection value | Interpretation |
|---|---|---|---|
| 1 | Human coronavirus HKU1 sample | 0.36 | Negative |
| 2 | Human coronavirus OC43 sample | 0.52 | Negative |
| 3 | Human coronavirus NL63 sample | 0.32 | Negative |
| 4 | Human coronavirus 229E sample | 0.16 | Negative |
| 5 | Novel A H1N1 influenza virus (2009) | 0.52 | Negative |
| 6 | Seasonal H1N1 influenza virus | 0.16 | Negative |
| 7 | H3N2 sample | 0.20 | Negative |
| 8 | H5N1 sample | 0.28 | Negative |
| 9 | H7N9 sample | 0.32 | Negative |
| 10 | Influenza B Yamagata positive sample | 0.32 | Negative |
| 11 | Influenza B Victoria positive sample | 0.16 | Negative |
| 12 | Human cytomegalovirus virus positive sample | 0.64 | Negative |
| 13 | Norovirus positive sample | 0.16 | Negative |
| 14 | Mumps virus positive sample | 0.48 | Negative |
| 15 | Normal human sample | 0.28 | Negative |
| 16 | | 0.44 | Negative |
| 17 | Novel coronavirus IgG antibody high positive sample | 0.40 | Negative |

It can be known from the above test results that when the above-mentioned samples that may cause cross-reactions and normal human samples were tested with this kit, and the test results were negative. It can be seen that the above-mentioned pathogen infection samples and normal human samples did not cross-react with this kit.

Test Example 4: The Influence of Substances That May Cause Interference on the Test Results The hemoglobin in clinical samples was mainly due to specimen hemolysis, including pathological hemolysis and technical hemolysis. Non-significant hemolysis meant that the hemoglobin content is less than 0.5 mg/mL, in which case hemolysis is not observed with the naked eye. The concentration of hemoglobin is 0.5 to 3 mg/mL in mild hemolysis, the concentration of hemoglobin is 3.1 to 5 mg/mL in moderate hemolysis, and the concentration of hemoglobin is >5 mg/mL in severe hemolysis. The experiment proved that when the hemoglobin concentration reached 7 mg/mL, the absolute value of the relative deviation of the test results did not exceed 10%, indicating that it did not interfere with the test results.

The range of bilirubin in normal human serum is 2 to 8 mg/L (the range of bilirubin in infants within 1 week is 10 to 120 mg/L). When the bilirubin concentration in the sample was as high as 300 mg/L, the absolute value of the relative deviation of the test results did not exceed 10%, indicating that it did not interfere with the test results.

The normal higher limit of triglycerides in clinical samples is 1.7 mmol/L. From the results of the experiment, when the triglyceride content in the samples was 7.5 mmoL/L, the absolute value of the relative deviation of the test results did not exceed 10%, indicating that it did not interfere with the test results.

In addition, substances that may cause interference such as rheumatoid factors, anti-nuclear antibodies, anti-double-stranded DNA antibodies, anti-mitochondrial antibodies, HAMA positive samples, novel coronavirus IgG antibody samples of high concentration, 50 g/L human total IgG antibody (total IgG amount of healthy adults: 7 to 16.6 g/L), and 10 g/L total human IgM antibody (total IgM amount of healthy adults: 400 to 3450 mg/L) had no effect on the test results.

Figure 2:
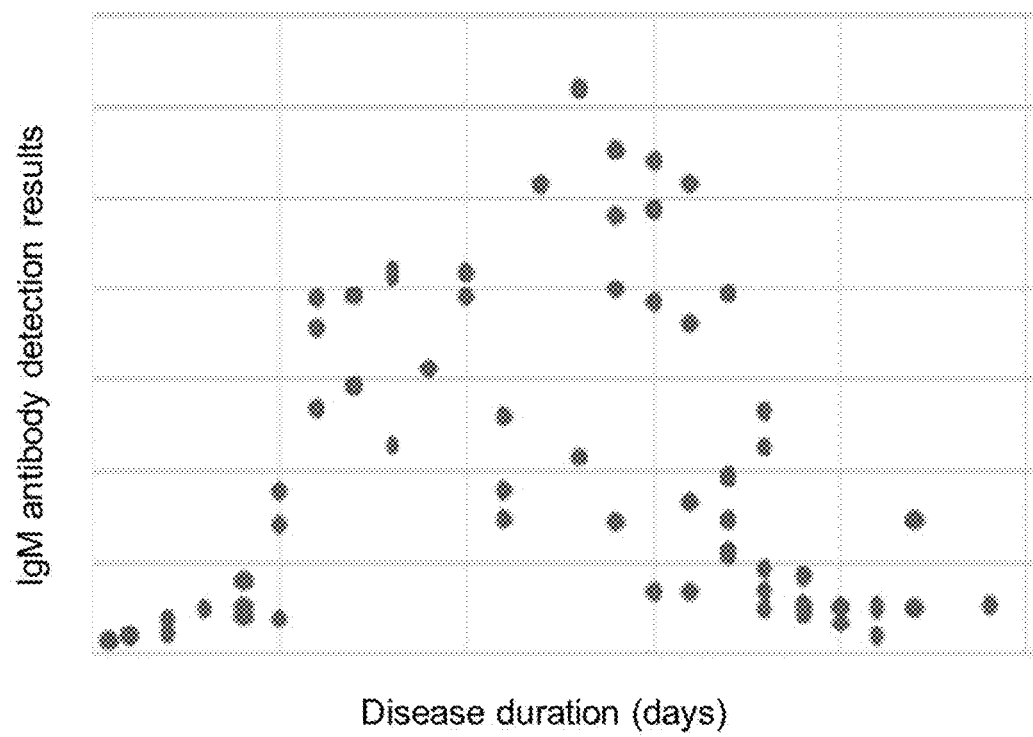
FIG. 2 is a scatter diagram showing the IgM antibody detection results in Test Example 5.

Test Example 5: Detection of Samples Sampled in Different Time Periods 65 confirmed samples with clear onset dates and sampling dates collected clinically were tested. The positive detection rates for different sampling periods were calculated. Then, a scatter plot of IgM antibody versus disease duration (days between the sampling date and the onset date) was plotted by taking disease duration as the abscissa and taking the I value of the sample detection result corresponding to the disease duration as the ordinate, as shown in FIG. 2.

The results are shown in Table 9 below.

TABLE 9

| Sampling period | Early stage (0 to 7 days) | Middle stage (8 to 14 days) | Late stage (≥15 days) |
|---|---|---|---|
| Positive detection rate in each period | 62.5% (10/16) | 100.0% (16/16) | 90.9% (30/33) |
| Total positive detection rate | | 86.2% (56/65) | |

From Table 9 and FIG. 1, it can be seen that the detection rate of IgM antibodies in the early stage of onset was 62.5%; IgM antibodies continued to increase with the duration of the disease; and the concentration of IgM antibodies reached a peak at 2 weeks, and gradually decreased with the duration of the disease.

Example 7

This example provided a novel coronavirus IgG antibody detection kit based on magnetic particle chemiluminescence, specifically comprising: streptavidin magnetic particles, biotin-labeled novel coronavirus antigens, an acridine sulfonamide-labeled goat anti-human IgG antibody, a sample diluent, a positive quality control material, a negative quality control material, a sample diluent and a washing solution.

(1) The preparation method of the biotin-labeled novel coronavirus antigen was as follows:

0.3 mg of nucleocapsid protein and 0.2 mg of spike protein S1 of the novel coronavirus were diluted with 0.02 M PBS (pH 7.2) buffer. The final concentration of the mixed antigens was 1 mg/mL.

12 μL of 10 mg/mL activated biotin was added to the above antigen buffer, mixed well, and kept at room temperature in the dark for 2 hours; and dialyzed against 0.02 M PBS buffer at 4° C. overnight to obtain a stock solution of the biotin-labeled antigens.

The working concentration of the biotin-labeled novel coronavirus antigens was 1 μg/mL.

(2) The preparation method of goat anti-human IgG antibody labeled with acridine sulfonamide was as follows:

0.2 mg of goat anti-human IgG antibody was placed in a glassware, and was diluted with 0.1 M CBS (pH 9.0) buffer to 1 mg/mL.

9.1 μL of 2 mg/mL NSP-SA-NHS solution was added to the above antibody diluent, mixed well, and kept at room temperature in the dark for 60 min.

Then 1.33 μL of 10% lysine solution was added, mixed well, kept at room temperature in the dark for 30 minutes; and dialyzed against 0.02 M PBS buffer solution at 4° C. overnight to obtain a stock solution of the acridine sulfonamide-labeled antibody.

The working concentration of acridine sulfonamide-labeled goat anti-human IgG antibody was 1 μg/mL.

Similarly, the IgG antibody detection kit also had high accuracy when detecting novel coronavirus. The test results obtained using it to test different samples are shown in Table 10 below.

TABLE 10

| | Kit Batch | | | | | |
|---|---|---|---|---|---|---|
| | Batch 1 | | Batch 2 | | Batch 3 | |
| Sample No. | I value in serum detection | I value in plasma detection | I value in serum detection | I value in plasma detection | I value in serum detection | I value in plasma detection |
| Negative 1 | 0.12 | 0.12 | 0.16 | 0.12 | 0.16 | 0.16 |
| Negative 2 | 0.24 | 0.28 | 0.24 | 0.20 | 0.24 | 0.20 |
| Negative 3 | 0.24 | 0.24 | 0.24 | 0.28 | 0.28 | 0.20 |
| Negative 4 | 0.32 | 0.36 | 0.36 | 0.32 | 0.32 | 0.32 |
| Negative 5 | 0.36 | 0.40 | 0.36 | 0.36 | 0.40 | 0.44 |
| Negative 6 | 0.36 | 0.40 | 0.36 | 0.32 | 0.40 | 0.36 |
| Negative 7 | 0.48 | 0.44 | 0.52 | 0.48 | 0.44 | 0.52 |
| Negative 8 | 0.56 | 0.56 | 0.52 | 0.60 | 0.60 | 0.64 |
| Negative 9 | 0.64 | 0.60 | 0.56 | 0.72 | 0.64 | 0.56 |
| Negative 10 | 0.64 | 0.68 | 0.64 | 0.68 | 0.52 | 0.56 |
| Positive 1 | 1.16 | 1.28 | 1.12 | 1.20 | 1.16 | 1.24 |
| Positive 2 | 1.40 | 1.40 | 1.44 | 1.36 | 1.40 | 1.48 |
| Positive 3 | 1.72 | 1.72 | 1.56 | 1.64 | 1.68 | 1.72 |
| Positive 4 | 1.84 | 1.76 | 1.96 | 1.88 | 1.80 | 1.88 |
| Positive 5 | 2.08 | 2.32 | 2.08 | 2.12 | 1.88 | 2.24 |
| Positive 6 | 2.32 | 2.40 | 2.20 | 2.36 | 2.24 | 2.32 |
| Positive 7 | 2.44 | 2.48 | 2.16 | 2.28 | 2.52 | 2.32 |
| Positive 8 | 3.20 | 3.08 | 2.96 | 3.24 | 3.24 | 3.24 |
| Positive 9 | 5.28 | 5.04 | 4.92 | 4.88 | 5.32 | 5.08 |
| Positive 10 | 6.72 | 7.36 | 6.32 | 6.72 | 7.00 | 6.44 |
| Positive 11 | 7.40 | 7.00 | 7.16 | 7.16 | 6.92 | 6.80 |
| Positive 12 | 8.28 | 8.44 | 8.48 | 8.36 | 8.40 | 8.04 |
| Positive 13 | 10.20 | 9.96 | 10.28 | 9.96 | 10.48 | 10.08 |

TABLE 10-continued

| | Kit Batch | | | | | |
| --- | --- | --- | --- | --- | --- | --- |
| | Batch 1 | | Batch 2 | | Batch 3 | |
| Sample No. | I value in serum detection | I value in plasma detection | I value in serum detection | I value in plasma detection | I value in serum detection | I value in plasma detection |
| Positive 14 | 11.20 | 11.84 | 11.80 | 10.24 | 11.20 | 10.96 |
| Positive 15 | 14.04 | 12.92 | 13.88 | 14.80 | 13.44 | 14.44 |
| Positive 16 | 16.92 | 18.08 | 14.96 | 16.12 | 16.76 | 15.52 |
| Positive 17 | 23.72 | 22.48 | 24.60 | 24.68 | 24.96 | 25.16 |
| Positive 18 | 25.88 | 24.96 | 27.32 | 27.20 | 24.56 | 26.68 |
| Positive 19 | 32.28 | 33.76 | 34.24 | 31.72 | 29.80 | 32.60 |
| Positive 20 | 46.08 | 46.84 | 44.80 | 44.08 | 47.72 | 45.00 |

It can be seen from the above table that the IgG antibody detection kit provided by this example can accurately detect, with good sensitivity and high accuracy.

In summary, the detection kit provided in the present application has good sensitivity in detecting both IgM antibodies and IgG antibodies. The IgM antibody detection kit has a lower limit of detection of 1:103, has high precision, high repeatability in multiple repeated tests, good specificity. It gives negative results for samples that may cause cross-reactions and normal human samples. Moreover, as for substances that may cause interference in the samples, the relative deviation of the detection results is controlled.

The applicant states that the above-mentioned is only particular embodiments of the present application, and the protection scope of the present application is not limited thereto. It should be apparent to those skilled in the art that any changes or substitutions that can be easily conceived by those skilled in the art within the technical scope disclosed in the present application all fall within the protection scope and the disclosed scope of the present application.

What is claimed is:

1. A novel coronavirus antibody detection kit based on magnetic particle chemiluminescence, comprising:
   streptavidin magnetic particles, biotin-labeled novel coronavirus antigens, an acridine sulfonamide-labeled secondary antibody, a sample diluent and a quality control material, wherein the biotin-labeled novel coronavirus antigens include a recombinant nucleocapsid protein and a recombinant spike protein S1;
   wherein, in the recombinant nucleocapsid protein, oligoproline residues are used to connect dominant epitopes of an original nucleocapsid protein, and oligolysine residues are used to form a C-terminus;
   in the recombinant spike protein S1, oligoproline residues are used to connect dominant epitopes of an original spike protein S1, and oligolysine residues are used to form a C-terminus;
   the recombinant nucleocapsid protein includes the amino acid sequence as shown in SEQ ID NO: 1; and
   the recombinant spike protein S1 includes the amino acid sequence as shown in SEQ ID NO: 3.

2. The novel coronavirus antibody detection kit according to claim 1, wherein the mass ratio of the recombinant nucleocapsid protein to the recombinant spike protein S1 is (1 to 3):1.

3. The novel coronavirus antibody detection kit according to claim 1, wherein in the biotin-labeled novel coronavirus antigen, the mass ratio of biotin to novel coronavirus antigen is (0.06 to 0.48):1.

4. The novel coronavirus antibody detection kit according to claim 1, wherein the sample diluent contains any one or a combination of at least two of bovine serum albumin, a rheumatoid factor adsorbent, a bacteriostatic agent, urea or a blocking agent.

5. The novel coronavirus antibody detection kit according to claim 1, wherein the quality control material includes a positive quality control material and a negative quality control material.

6. The novel coronavirus antibody detection kit according to claim 1, wherein the novel coronavirus antibody detection kit further comprises an excitation solution and a washing solution.

7. A method for preparing the novel coronavirus antibody detection kit of claim 1, comprising:
   (1) preparing biotin-labeled novel coronavirus antigens: mixing nucleocapsid protein and spike protein S1 of novel coronavirus as antigens with a PBS buffer, adding activated biotin and labeling for 1.5 to 2.5 hours, and then dialyzing to obtain the biotin-labeled novel coronavirus antigens;
   (2) preparing an acridine sulfonamide-labeled secondary antibody: mixing a secondary antibody with a CBS (Carbonate-Buffered Saline) buffer, adding acridine sulfonamide and labeling for 0.5 to 1.5 h, then adding a lysine solution, and dialyzing to obtain the acridine sulfonamide-labeled secondary antibody; and
   (3) packaging the biotin-labeled novel coronavirus antigens, the acridine sulfonamide-labeled secondary antibody, streptavidin magnetic particles, a sample diluent and a quality control material, separately, to obtain the novel coronavirus antibody detection kit.

8. A method for using the novel coronavirus antibody detection kit according to claim 1, comprising the following steps:
   adding biotin-labeled novel coronavirus antigens and streptavidin magnetic particles to a sample to be tested, performing a first incubation, washing, then adding the acridine sulfonamide-labeled secondary antibody, performing a second incubation, washing, and then detecting to obtain detected results.

9. The method according to claim 8, wherein the sample to be tested is serum or plasma;
   the sample to be tested is diluted with a sample diluent;
   the titer ratio of the sample to be tested after dilution is 1:(103 to 110);
   the volume ratio of the sample to be tested, the biotin-labeled novel coronavirus antigens and streptavidin magnetic particles is (50 to 100):(25 to 75):(30 to 50);
   the working concentration of the acridine sulfonamide-labeled secondary antibody is 0.125 to 1 µg/mL;
   the first incubation is carried out for 5 to 15 min; and
   the second incubation is carried out for 5 to 15 min.

* * * * *